United States Patent

Kogiso et al.

[11] Patent Number: 6,136,956
[45] Date of Patent: Oct. 24, 2000

[54] FIBROUS ASSEMBLY OF PEPTIDE LIPID AND METHOD FOR THE PREPARATION THEREOF

[75] Inventors: Masaki Kogiso; Toshimi Shimizu, both of Tsukuba, Japan

[73] Assignee: Japan as represented by Director General of Agency of Industrial Science and Technology, Tokyo-to, Japan

[21] Appl. No.: 09/261,156

[22] Filed: Mar. 3, 1999

[30] Foreign Application Priority Data

Mar. 13, 1998 [JP] Japan .................................. 10-062548

[51] Int. Cl.$^7$ ........................... C07K 16/00; A61K 38/00

[52] U.S. Cl. ........................ 530/359; 530/331; 530/333; 530/343; 514/18; 514/19

[58] Field of Search .................................... 530/359, 331, 530/333, 343; 514/18, 19

[56] References Cited

PUBLICATIONS

O. Träet al., *J. Am. Chem. Soc.*, 119, 9120–9124 (1997).

*Primary Examiner*—Christopher S. F. Low
*Assistant Examiner*—Abdel A. Mohamed
*Attorney, Agent, or Firm*—Wenderoth, Lind & Ponack, L.L.P.

[57] ABSTRACT

Disclosed is a fine fibrous assembly having a molecular structure of a bola-form peptide lipid containing L- or D-valine residues which can be obtained by spontaneous crystallization precipitation when an aqueous solution of the peptide lipid compound of the general formula

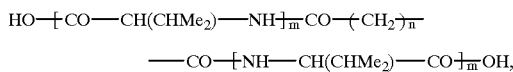

in which Me is a methyl group, the subscript m is 1, 2 or 3 and the subscript n is a positive integer in the range from 6 to 18, in the form of an alkali metal salt is kept standing over days under an atmosphere of a saturated vapor over a dilute aqueous solution of a vaporizable acid such as acetic acid.

7 Claims, 2 Drawing Sheets

FIBROUS ASSEMBLY OF PEPTIDE LIPID AND METHOD FOR THE PREPARATION THEREOF

BACKGROUND OF THE INVENTION

The present invention relates to a novel fibrous assembly of a peptide lipid or, more particularly, to an assembly of fibers formed from a metal salt of a self-assembling bola-form peptide lipid having two oligo-L-valine residues or oligo-D-valine residues at both molecular terminals as well as to a method for the preparation of such a fibrous assembly.

As is well known, fibrous assemblies of a peptide lipid are widely employed in many applications, besides the applications as a drug delivery system or an adsorbent, in the fields of medical and pharmaceutical sciences as a bioadaptable material, in the fields of electronic and information-processing technologies as a material of microelectronic parts, in the fields of food industries, agriculture, forestry and fiber industries as an emulsifying agent, stabilizer, dispersing agent or moisturizing agent and so on.

In the prior art, spherical assemblies obtained from a natural phospholipid or so-called liposomes are known among molecular aggregates formed from a phospholipid. Such a spherical assembly is usually prepared by the thin-film method, thermal dispersion method, cholic acid method or reversed-layer evaporation method (see, for example, "Seitaimaku Jikkenhou" (Experimental Methods for Biomembranes), volume 2, page 185, published by Kyoritu Shuppan Co.).

Each of these prior art methods, however, requires extremely high skillfullness. In addition, the molecular aggregates obtained by these methods are limited to a monolayered vesicle or spherical multilayered vesicle and long fibrous assemblies cannot be prepared thereby. On the other hand, several method are disclosed, for example, in Journal of the American Chemical Society, volume 119, pages 9120–9124 (1997) for the preparation of a fibrous assembly from a synthetic amphiphilic compound in water. Each of these methods, however, is a method in which fibrous assemblies are obtained by spontaneous precipitation or crystallization from a hot concentrated aqueous solution containing an amphiphilic compound so that the yield of the product is necessarily limited.

SUMMARY OF THE INVENTION

The present invention accordingly has an object, in view of the above described problems in the prior art, to provide a novel fibrous assembly of a peptide lipid having a length of several micrometers and a diameter of several tens of nanometers, which could never be obtained in the prior art from a natural phospholipid.

Thus, the fibrous assembly of a peptide lipid provided by the present invention is formed from an alkali metal salt, e.g., lithium salt, sodium salt and potassium salt, of a bola-form peptide lipid represented by the general formula

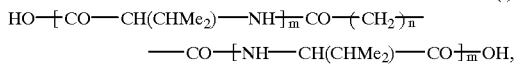

in which Me is a methyl group, the subscript m is 1, 2 or 3 and the subscript n is a positive integer in the range from 6 to 18.

In particular, the valine units forming the peptide lipid molecule of the general formula (I) all have the same stereo-isomeric structure of the L-body or D-body.

According to the invention, the above defined fibrous assembly is prepared by a method which comprises the steps of:

(a) dissolving an alkali metal salt of a bola-form peptide lipid represented by the above given general formula (I) in water to give an aqueous solution; and (b) standing the aqueous solution under a slightly acidified atmosphere of a saturated vapor of an aqueous acid solution such as an aqueous acetic acid solution in a concentration of 1 to 5% by weight.

DETAILED DESCRIPTION OF THE PREFERRED EMBODIMENTS

Figure 1:
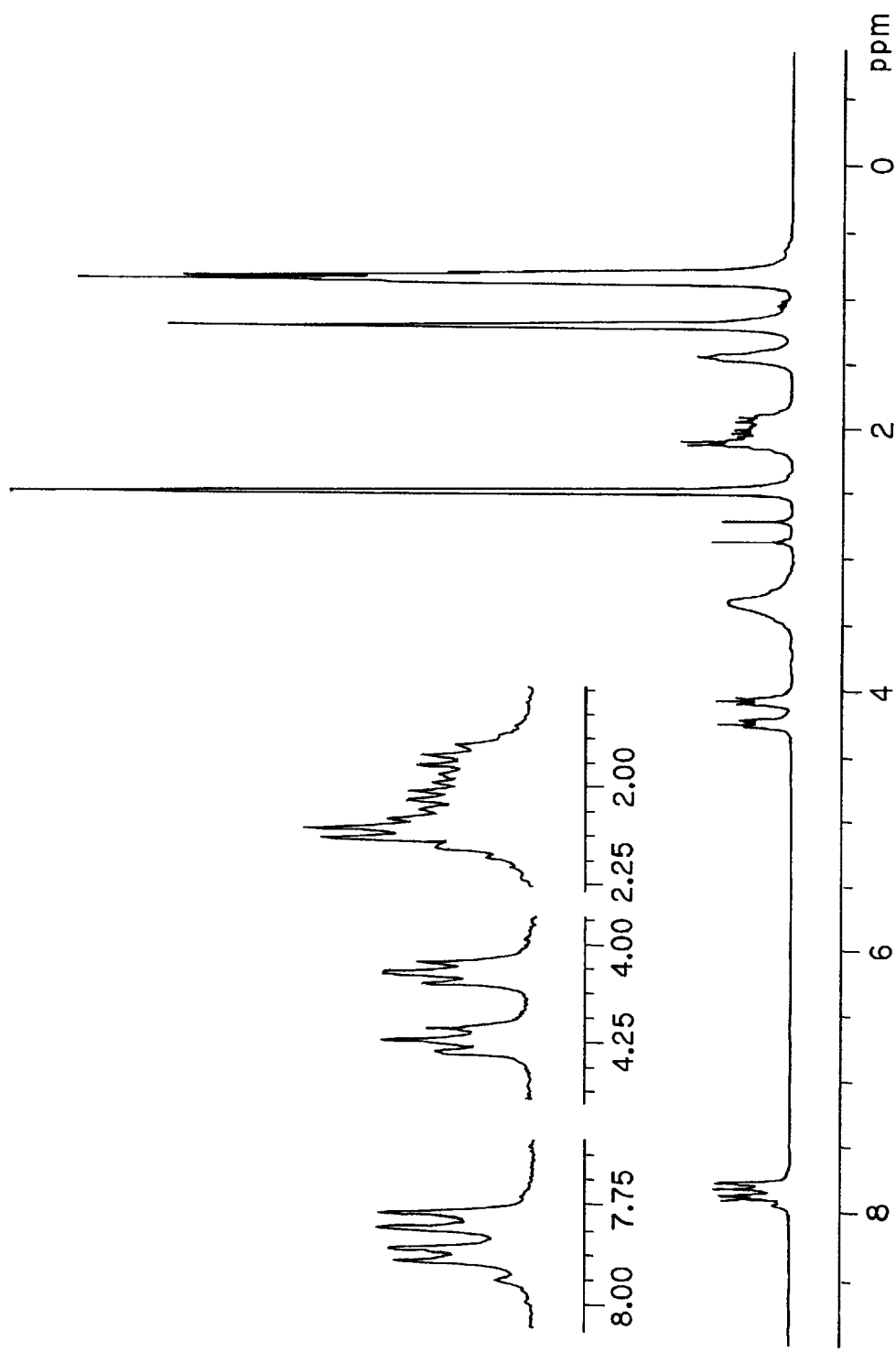
FIG. 1 is a $^1$H-NMR spectrum of the peptide lipid compound prepared in Reference Example 3.

As is described above, the fibrous assembly of the invention is constituted from molecules of a bola-form peptide lipid containing valine residues represented by the general formula (I). Such a unique fibrous assembly is obtained when an aqueous solution of the peptide lipid compound in the form of an alkali metal salt is kept standing under a slightly acidified atmosphere of a saturated vapor of an aqueous solution of a weak acid so that growth of a fibrous crystalline assembly proceeds in the aqueous solution of the peptide lipid.

The bola-form peptide lipid represented by the general formula (I) has a structure with two optically active L-valine residues or D-valine residues or oligomeric residues thereof connected to the carboxylic groups of a long-chain dicarboxylic acid by forming an amide linkage having the C-terminals of an oligopeptide at both molecular terminals. It is essential that the valine residues forming the oligopeptide chain all have the same optical activity of either the D-body or the L-body. When valine residues of different optical activities are contained in the molecule, the inventive method fails to produce a fine fibrous assembly but amorphous particles are formed in the aqueous solution of the starting material. The value of the subscript m in the general formula (I) is limited not to exceed 3 because, when m is 4 or larger, the solubility of the peptide lipid compound in water is decreased to cause difficulties in the preparation of a fibrous assembly.

The subscript n, which gives the chain length of the linear alkylene group or polymethylene chain, is a positive integer of 6 to 18. Namely, the polymethylene group is exemplified by hexylene, heptylene, octylene, nonylene, decylene, undecylene, dodecylene, tetradecylene, hexadecylene and octadecylene groups. When the value of n is too small, fine fibrous assemblies can hardly be obtained by undertaking the inventive method while, when n is too large, the precipitates formed in the aqueous medium are in the form of amorphous particles.

The bola-form peptide lipid compound represented by the general formula (I) is a novel compound not reported in any literatures. This compound can readily be prepared by the following synthetic method. Thus, an oligo-L-valine or oligo-D-valine having an unprotected N-terminal and protected C-terminal in the form of a hydrochloride as represented by the general formula

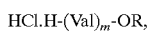 (II)

in which R is a protective group to the C-terminal of an amino acid, Val is an L- or D-valine residue and m is 1, 2 or 3, is reacted with a dicarboxylic acid represented by the general formula

(III)

to effect a dehydration condensation reaction followed by elimination of the protective groups R to give the desired bola-form peptide lipid compound of the general formula (I).

Following is a typical procedure for the preparation of the oligo-L- or oligo-D-valine hydrochloride having an unprotected N-terminal and protected C-terminal represented by the general formula (II) to be used as one of the starting materials in the preparation of the peptide lipid compound. When the compound is a tripeptide, in particular, an L- or D-valine compound having a protected amino group is reacted with an L-valine or D-valine, respectively, having a protected carboxyl group to give a dipeptide compound which is, after elimination of the amino-protective group, again reacted with L-valine or D-valine, respectively, having a protected amino group to give a tripeptide compound from which the N-protective group is eliminated. The C-terminal-protective group R in the general formula (II) is exemplified by methyl, ethyl, benzyl, p-nitrobenzyl, p-methoxybenzyl and tert-butyl groups.

The various reagents, i.e. amino group-protective agent, carboxyl group-protective agent and coupling agent, and the procedures in the above described reaction can be conventional and freely selected from those used in the prior art for peptide synthesis. The intermediate peptide compounds formed in the course of the reaction can readily be isolated and purified by washing the reaction mixture with an acid or alkali aqueous solution followed by recrystallization or reprecipitation.

Examples of the dicarboxylic acid represented by the general formula (III) to be used as a reactant of the dehydration condensation reaction include suberic acid, azelaic acid, sebacic acid, 1,9-nonane dicarboxylic acid, 1,10-decane dicarboxylic acid, 1,11-undecane dicarboxylic acid, 1,12-dodecane dicarboxylic acid, 1,13-tridecane dicarboxylic acid, 1,14-tetradecane dicarboxylic acid, 1,16-hexadecane dicarboxylic acid and 1,18-octadecane dicarboxylic acid.

The bola-form peptide lipid of the general formula (I) obtained in the above described manner is usually a white solid at room temperature.

The fine fibrous assembly of the invention is obtained from an aqueous solution of an alkali metal salt of the above described bola-form peptide lipid compound by causing precipitation thereof in a crystalline form.

The aqueous solution of an alkali metal salt of the peptide lipid compound is prepared by dissolving the peptide lipid compound in a 5 to 20 mmoles/liter aqueous solution of an alkali metal hydroxide, which is preferably lithium hydroxide, sodium hydroxide or potassium hydroxide, in an amount substantially equal to two moles per mole of the bola-form peptide lipid compound. When the concentration of the alkali metal hydroxide in the aqueous solution is too high, the precipitates formed in the solution are rather in the form of an amorphous solid while, when the concentration is too low, a fine fibrous assembly can hardly be obtained. The metal salt dissolved in the aqueous solution is limited to an alkali metal salt because, when the alkali metal salt is replaced with an alkaline earth metal salt, the precipitates formed in the aqueous solution are in the form of an amorphous solid and not in the form of a fine fibrous assembly.

In the method of the present invention, the aqueous solution containing a bola-form peptide lipid compound in the form of an alkali metal salt is kept standing under a slightly acidic atmosphere of a saturated vapor of an aqueous solution of a weak acid so that unidirectional self-assembling of the peptide lipid compound proceeds in the solution to give the desired fine fibrous assembly. The slightly acidic atmosphere of a saturated vapor can advantageously be formed by using a diluted aqueous solution of an acid having adequate volatility in a concentration of 1 to 5% by weight. The acid to form the diluted aqueous acid solution is exemplified, preferably, by acetic acid, dichloroacetic acid, formic acid and carbonic acid either singly or as a combination of two kinds or more. When the concentration of the aqueous acid solution is too high, the precipitates formed in the aqueous solution of the starting peptide lipid compound are in the form of an amorphous solid not to give a fine fibrous assembly while, when the concentration of the acid is too low, the desired fine fibrous assembly sometimes fails to be formed in the aqueous medium. Gelation of an aqueous solution of the starting peptide lipid compound is observed when the solution is kept standing under an atmosphere over a 1% by weight aqueous solution of acetic acid for 1 to 2 weeks. The thus gelled aqueous solution of the starting peptide lipid compound contains fine fibrous assemblies having a length of several micrometers and a diameter of several tens of nanometers which can be detected by the examination with a transmission or scanning electron microscope. Such a fine fibrous assembly of a peptide lipid compound can never be obtained from natural phospholipids.

In the following, the present invention is described in more detail by way of Examples as preceded by Reference Examples for the preparation of the peptide lipid compounds used as the starting material in the inventive method, although the scope of the invention is never limited in any way by these Examples and Reference Examples.

The Rf values in the thin-layer chromatography described below were given as Rf1 and Rf2 when the developing solvent was a 5:1 by volume mixture of chloroform and methyl alcohol or a 95:5:1 by volume mixture of chloroform, methyl alcohol and acetic acid, respectively.

REFERENCE EXAMPLE 1

A solution was prepared by dissolving, in 150 ml of dichloromethane, 10.9 g (50.0 mmoles) of tert-butyloxycarbonyl-L-valine, 19.0 g (50.0 mmoles) of L-valine benzyl ester p-toluenesulfonate and 7.0 ml (50.0 mmoles) of triethylamine and the solution under agitation at −5° C. was admixed with 100 ml of a dichloromethane solution containing 10.5 g (55.0 mmoles) of 1-ethyl-3-(3-dimethylaminopropyl) carbodiimide hydrochloride as a water-soluble carbodiimide compound to form a reaction mixture which was agitated for 24 hours at −5° C. The dichloromethane solution as the reaction mixture was then washed successively each twice with a 10% by weight aqueous solution of citric acid, pure water, a 4% by weight aqueous solution of sodium hydrogencarbonate and pure water followed by drying of the organic solution over anhydrous sodium sulfate. The thus dried reaction mixture was then completely freed from the solvent by distillation under reduced pressure to give a clear and colorless oil, which was tert-butyloxycarbonyl-L-valyl-L-valine benzyl ester. This oily product was dissolved in 100 ml of ethyl acetate and the solution was admixed with 120 ml of a 4 moles/liter ethyl acetate solution of hydrogen chloride and agitated for 4 hours. The solution was completely freed from the solvent by distillation under reduced pressure to give white precipitates which were collected and thoroughly washed with diethyl ether to give 13.8 g of a white solid having Rf values in the thin-layer chromatography of Rf1=0.58 and Rf2=0.05 and a melting point of 182–183° C., which could be identified to be L-valyl-L-valine benzyl ester hydrochloride. The above mentioned yield of the product was 80% of the theoretical value.

REFERENCE EXAMPLE 2

A solution was prepared by dissolving, in 300 ml of dichloromethane, 5.43 g (25 mmoles) of tert-butyloxycarbonyl-L-valine, 5.18 g (25 mmoles) of the L-valyl-L-valine benzyl ester hydrochloride obtained in Reference Example 1 and 3.5 ml (25 mmoles) of triethylamine and the solution under agitation at −5° C. was admixed with 50 ml of a dichloromethane solution containing 5.27 g (27.5 mmoles) of 1-ethyl-3-(3-dimethylaminopropyl) carbodiimide hydrochloride to form a reaction mixture which was agitated for 24 hours. The dichloromethane solution was then washed successively each twice with a 10% by weight aqueous solution of citric acid, pure water, a 4% by weight aqueous solution of sodium hydrogencarbonate and pure water followed by drying of the organic solution over anhydrous sodium sulfate. The thus dried reaction mixture was then completely freed from the solvent by distillation under reduced pressure to give a light yellow oil, which was tert-butyloxycarbonyl-L-valyl-L-valyl-L-valine benzyl ester. This oily product was dissolved in 100 ml of ethyl acetate and the solution was admixed with 60 ml of a 4 moles/liter ethyl acetate solution of hydrogen chloride and agitated for 4 hours. The solution was then freed from the solvent by distillation under reduced pressure to give 9.28 g of a colorless oil having Rf values in the thin-layer chromatography of Rf1=0.25 and Rf2=0.05, which could be identified to be L-valyl-L-valyl-L-valine benzyl ester hydrochloride. The above mentioned yield of the product was 84% of the theoretical value.

REFERENCE EXAMPLE 3

A solution was prepared by dissolving, in 10 ml of N,N-dimethylformamide, 0.46 g (2 mmoles) of 1,10-decane dicarboxylic acid and 0.674 g (4.4 mmoles) of 1-hydroxybenzotriazole and the solution under agitation at −5° C. was admixed with 10 ml of a dichloromethane solution containing 0.90 g (4.4 mmoles) of 1-ethyl-3-(3-dimethylaminopropyl) carbodiimide hydrochloride. After 1 hour therefrom, the reaction mixture was admixed with 10 ml of a dichloromethane solution containing 1.51 g (4.4 mmoles) of the L-valyl-L-valine benzyl ester hydrochloride obtained in Reference Example 1 and then with 0.62 ml (4.4 mmoles) of triethylamine and was agitated for further 24 hours while the temperature was gradually increased to room temperature. The reaction mixture was then completely freed from the solvent under reduced pressure and the white precipitates on the filter paper were washed successively with 50 ml of a 10% by weight aqueous solution of citric acid, 20 ml of pure water, 50 ml of a 4% by weight aqueous solution of sodium hydrogencarbonate and 20 ml of pure water to give 0.98 g (61% of the theoretical yield) of a white solid which was identified to be N,N'-bis(L-valyl-L-valine benzyl ester)decane-1,10-dicarboxamide.

In the next place, 0.5 g (0.62 mmole) of the dicarboxamide compound was dissolved in 100 ml of N,N-dimethylformamide with addition of 0.25 g of a palladium/carbon catalyst containing 10% by weight of palladium and a catalytic hydrogen reducing reaction of the compound was undertaken for 6 hours. The reaction mixture was then freed from the catalyst particles by filtration using Celite followed by removal of the solvent by distillation under reduced pressure to give a colorless oil, from which 0.39 g of a white solid product was obtained by recrystallization from a mixed solvent of water and ethyl alcohol. This solid product having a melting point of 132–136° C. could be identified to be N,N'-bis(L-valyl-L-valine)decane-1,10-dicarboxamide and the above mentioned yield of the product was almost theoretical.

The results of the elementary analysis of this product were as follows.

Calculated, %, as $C_{32}H_{58}O_8N_4 \cdot 0.5H_2O$: C 60.44; H 9.35; N 8.81

Found, %: C 60.24; H 9.27; N 8.97

FIG. 1 of the accompanying drawing shows a $^1$H-NMR spectrum of this compound in dimethylsulfoxide-$d_6$.

EXAMPLE 1

A 62.7 mg (0.1 mmole) portion of the N,N'-bis(L-valyl-L-valine)decane-1,10-dicarboxamide prepared in Reference Example 3 described above was introduced into a glass vial to which 10 ml of an aqueous solution containing 8.0 mg (0.20 mmole) of sodium hydroxide were added. The dicarboxamide compound as a bola-form peptide lipid was dissolved in the aqueous alkali solution under bath-type ultrasonic irradiation.

The aqueous solution was kept standing at room temperature for 2 weeks under an atmosphere of a saturated vapor over a 1% by weight aqueous solution of acetic acid to find gelation of the solution. When the atmosphere was filled with a saturated vapor over a 5% by weight aqueous solution of acetic acid, gelation of the aqueous solution was complete within 5 days.

Figure 2:
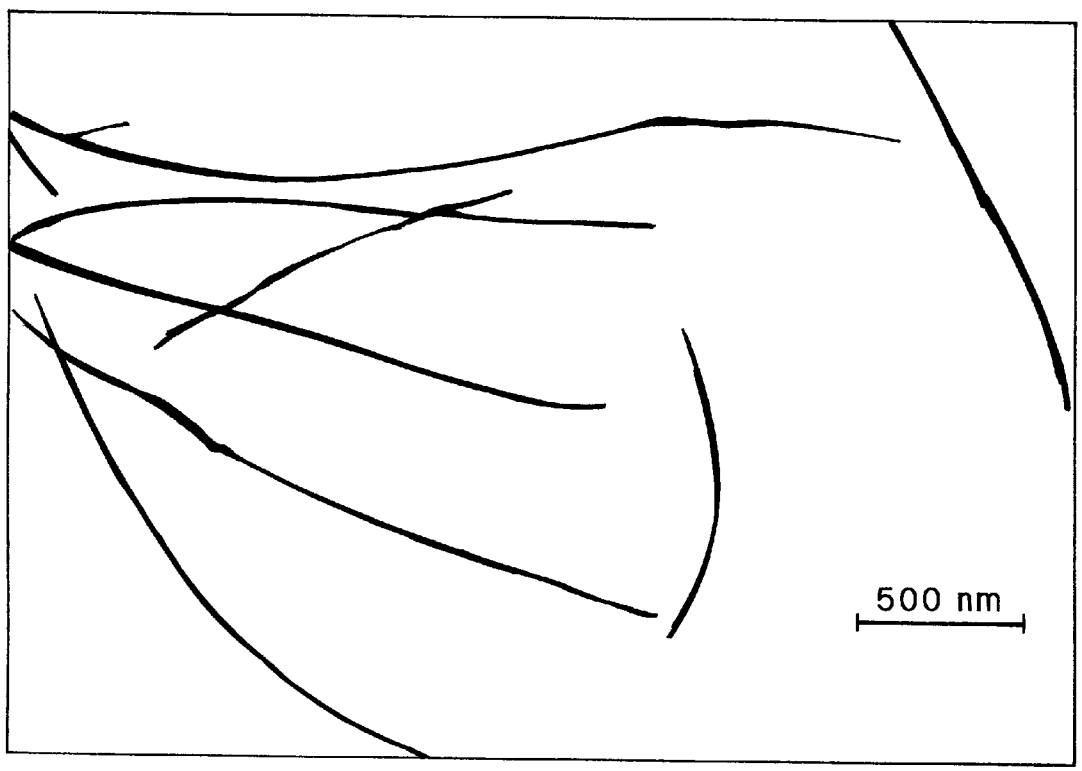
FIG. 2 is a sketch from a transmission electron microscopic photograph of the fibrous assembly prepared in Example 1.

The thus gelled aqueous solution was examined on a transmission electron microscope to detect fine fibrous assemblies having a length of several micrometers and a diameter of several tens of nanometers as is illustrated in FIG. 2 which is a sketch of the transmission electron microscopic photograph of the fibrous assemblies.

EXAMPLE 2

A 59.9 mg (0.1 mmole) portion of N,N'-bis(L-valyl-L-valine)octane-1,8-dicarboxamide, which was prepared in substantially the same manner as in Reference Example 3 by the coupling reaction of L-valyl-L-valine benzyl ester hydrochloride and 1,8-octane dicarboxylic acid in place of 1,10-decane dicarboxylic acid, was taken in a glass vial together with 10 ml of an aqueous solution containing 8.0 mg (0.2 mmole) of sodium hydroxide and the bola-form peptide lipid compound was dissolved in the aqueous alkali solution under ultrasonic irradiation.

The aqueous solution was kept standing at room temperature for 3 weeks under an atmosphere of a saturated vapor over a 2% by weight aqueous solution of acetic acid to find gelation of the solution. When the atmosphere was filled with a saturated vapor over a 5% by weight aqueous solution of acetic acid, gelation of the aqueous solution was complete within a week.

The thus gelled aqueous solution was examined on a transmission electron microscope to detect fine fibrous assemblies having a length of several micrometers and a diameter of several tens of nanometers.

EXAMPLE 3

A 57.1 mg (0.1 mmole) portion of N,N'-bis(L-valyl-L-valine)hexane-1,6-dicarboxamide, which was prepared in substantially the same manner as in Reference Example 3 by the coupling reaction of L-valyl-L-valine benzyl ester hydrochloride and 1,6-hexane dicarboxylic acid in place of 1,10-decane dicarboxylic acid, was taken in a glass vial together with 10 ml of an aqueous solution containing 8.0 mg (0.2 mmole) of sodium hydroxide and the bola-form peptide lipid compound was dissolved in the aqueous alkali solution under ultrasonic irradiation.

The aqueous solution was kept standing at room temperature for 3 weeks under an atmosphere of a saturated vapor over a 1% by weight aqueous solution of acetic acid to find gelation of the solution.

The thus gelled aqueous solution was examined on a transmission electron microscope to detect fine fibrous assemblies having a length of several micrometers and a diameter of several tens of nanometers.

EXAMPLE 4

A 73.9 mg (0.1 mmole) portion of N,N'-bis(L-valyl-L-valine)octadecane-1,18-dicarboxamide, which was prepared in substantially the same manner as in Reference Example 3 by the coupling reaction of L-valyl-L-valine benzyl ester hydrochloride and 1,18-octadecane dicarboxylic acid in place of 1,10-decane dicarboxylic acid, was taken in a glass vial together with 10 ml of an aqueous solution containing 8.0 mg (0.2 mmole) of sodium hydroxide and the bola-form peptide lipid compound was dissolved in the aqueous alkali solution under ultrasonic irradiation.

The aqueous solution was kept standing at room temperature for 3 weeks under an atmosphere of a saturated vapor over a 1% by weight aqueous solution of acetic acid to find gelation of the solution.

The thus gelled aqueous solution was examined on a transmission electron microscope to detect fine fibrous assemblies having a length of several micrometers and a diameter of several tens of nanometers.

EXAMPLE 5

A 82.5 mg (0.1 mmole) portion of N,N'-bis(L-valyl-L-valyl-L-valine)decane-1,10-dicarboxamide, which was prepared in substantially the same manner as in Reference Example 3 by the coupling reaction of 1,10-decane dicarboxylic acid and L-valyl-L-valyl-L-valine benzyl ester hydrochloride in place of L-valyl-L-valine benzyl ester hydrochloride, was taken in a glass vial together with 10 ml of an aqueous solution containing 8.0 mg (0.2 mmole) of sodium hydroxide and the bola-form peptide lipid compound was dissolved in the aqueous alkali solution under ultrasonic irradiation.

The aqueous solution was kept standing at room temperature for a week under an atmosphere of a saturated vapor over a 1% by weight aqueous solution of acetic acid to find gelation of the solution.

The thus gelled aqueous solution was examined on a transmission electron microscope to detect fine fibrous assemblies having a length of several micrometers and a diameter of several tens of nanometers.

EXAMPLE 6

A 62.7 mg (0.1 mmole) portion of N,N'-bis(D-valyl-D-valine)decane-1,10-dicarboxamide, which was prepared in substantially the same manner as in Reference Example 3 by the coupling reaction of 1,10-decane dicarboxylic acid and D-valyl-D-valine benzyl ester hydrochloride in place of L-valyl-L-valine benzyl ester hydrochloride, was taken in a glass vial together with 10 ml of an aqueous solution containing 8.0 mg (0.2 mmole) of sodium hydroxide and the bola-form peptide lipid compound was dissolved in the aqueous alkali solution under ultrasonic irradiation.

The aqueous solution was kept standing at room temperature for three weeks under an atmosphere of a saturated vapor over a 2% by weight aqueous solution of acetic acid to find gelation of the solution. When the atmosphere was filled with a saturated vapor over a 5% by weight aqueous solution of acetic acid, gelation of the aqueous solution was complete within a week.

The thus gelled aqueous solution was examined on a transmission electron microscope to detect fine fibrous assemblies having a length of several micrometers and a diameter of several tens of nanometers.

What is claimed is:

1. A fibrous assembly of a peptide lipid formed from a bola-form peptide lipid having valine units as represented by the general formula

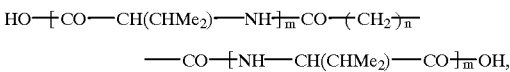

in which Me is a methyl group, the subscript m is 1, 2 or 3 and the subscript n is a positive integer in the range from 6 to 18.

2. The fibrous assembly of a peptide lipid as claimed in claim 1 in which the valine units all have the same stereoisomeric structure of the L-valine or D-valine.

3. A method for the preparation of a fibrous assembly of a peptide lipid formed from a bola-form peptide lipid having valine units as represented by the general formula

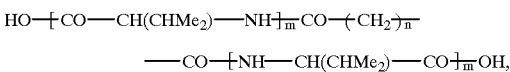

in which Me is a methyl group, the subscript m is 1, 2 or 3 and the subscript n is a positive integer in the range from 6 to 18 which comprises the steps of:

(a) dissolving a bola-form peptide lipid represented by the above given general formula in an aqueous solution of an alkali metal hydroxide to give an aqueous solution of the bola-form peptide lipid in the form of an alkali metal salt; and (b) standing the aqueous solution under an acidified atmosphere of a saturated vapor of an aqueous solution of an acid in a concentration of 1 to 5% by weight.

4. The method for the preparation of a fibrous assembly of a peptide lipid as claimed in claim 3 in which the valine units in the bola-form peptide lipid all have the same stereoisomeric structure of the L-valine or D-valine.

5. The method for the preparation of a fibrous assembly of a peptide lipid as claimed in claim 3 in which the alkali metal hydroxide is lithium hydroxide, sodium hydroxide or potassium hydroxide.

6. The method for the preparation of a fibrous assembly of a peptide lipid as claimed in claim 3 in which the acid is acetic acid.

7. The method for the preparation of a fibrous assembly of a peptide lipid as claimed in claim 3 in which the concentration of the alkali metal hydroxide in the aqueous solution in step (a) is in the range from 5 to 20 mmoles/liter.

* * * * *